(12) United States Patent
Uang et al.

(10) Patent No.: US 6,258,966 B1
(45) Date of Patent: Jul. 10, 2001

(54) CHIRAL LIGAND AND METHOD FOR PREPARING CYANOHYDRINS FROM ALDEHYDES

(75) Inventors: Biing-Jiun Uang, Taipei; Chun-Tzu Yang, Taipei Hsien, both of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/417,206

(22) Filed: Oct. 13, 1999

(51) Int. Cl.$^7$ .............................. C07F 7/00; C07C 233/00; C07C 253/00
(52) U.S. Cl. ............................ 556/54; 564/155; 564/158; 558/351; 556/56
(58) Field of Search ..................................... 564/123, 124, 564/152, 155, 158; 556/54, 56; 558/351

(56) References Cited

PUBLICATIONS

Chyuan–Der Hwang et al, Enantioselective addition of trimethylsilyl cyanide, Journal of Organic chemistry (1998), 63 (20), 6762–6763, 1998.*

* cited by examiner

*Primary Examiner*—Paul J. Killos
*Assistant Examiner*—J. Parsa
(74) *Attorney, Agent, or Firm*—Bacon & Thomas, PLLC

(57) ABSTRACT

A chiral ligand of the formula (II) or formula (II'),

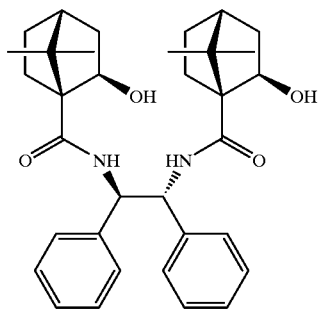
(II)

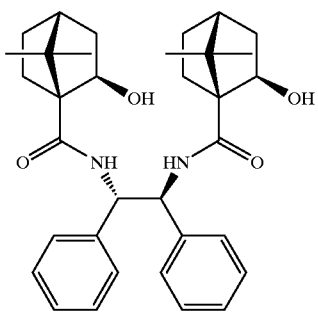

(II')

was synthesized. The chiral ligand (II) or formula (II') can chelate to metals to form a catalytic complex to catalyze the addition of trimethylsilyl cyanide to aldehydes to give optically active cyanohydrin, individually.

5 Claims, No Drawings

CHIRAL LIGAND AND METHOD FOR PREPARING CYANOHYDRINS FROM ALDEHYDES

FIELD OF THE INVENTION

The present invention relates to a chiral ligand, especially relates to a novel chiral ligand to complex with Ti $(O^iPr)_4$ to catalyze the asymmetric addition of trimethylsilyl cyanides to aldehydes to give optically active hydroxylcyanides.

BACKGROUND OF THE INVENTION

Optically pure cyanohydrins are versatile synthetic intermediates, the two functional groups being easily manipulated into a wide range of other chiral products such as α-hydroxy acids, α-hydroxy aldehydes, α-hydroxy ketones, β-hydroxy amines and α-amino acid derivatives etc.

The usual synthetic route to cyanohydrins was invented more than one hundred years ago. However, the cyanohydrin produced by this well known way is a racemic product. If optically active cyanohydrins are required for further asymmetric synthesis, additional resolution steps for the racemic cyanohydrin would be needed. To overcome this problem, several asymmetrical synthesis of cyanohydrin have been developed. Most of these asymmetric syntheses used a chiral catalyst to induce the formation of just one enantiomer of the cyanohydrin. So far, a number of different catalyses have been investigated, including enzymes, polymeric reagents, peptides and organometallic species. Among them, organometallic species are the catalysts developed most recently.

Organometallic species, which were used as the catalyses to catalyze the asymmetric addition of trimethylsilyl cyanide to aldehydes, were disclosed in several technical literatures. However, drawbacks could also be found among these organometallic species. For example, the organometallic complexes of binaphthaol and titanium tetraisopropoxide, reported by Nakai et al., have enantioselectivity only for aromatic aldehydes. The organometallic complexes reported by Jiang et al. have enantioselectivity but are easily deteriorated by acids. Bolm et al. also reported organometallic complexes with good enantioselectivity, but stoichiometric amounts of the organometallic complexes catalyst were required.

The inventor Uang et al. disclosed new ligands, i.e. ligand(I) and ligand (I'),

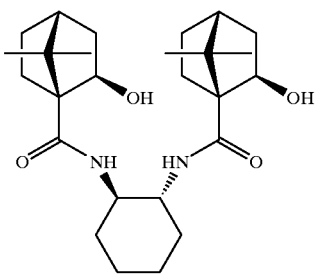

(I)

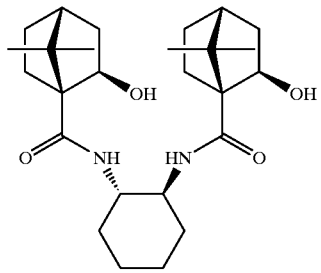

(I')

that can complex with titanium tetraisopropxide [Ti(O$^i$Pr)$_4$] to form catalysts of the addition of trimethylsilyl cyanide to benzaldehyde in the pending patent application (application no. TW 87112176). The organometallic complexes catalyst containing chiral ligand (I) has acceptable enantioselectivities for all kinds of aldehydes. In particular, high enantioselectivities can be observed for aliphatic aldehydes. As used for catalyzing the synthesis of the asymmetric addition of trimethylsilyl cyanide to aldehydes to give optically active cyanohydrins, only catalytic amounts of the chiral ligand (I) (or (I')) are required. Although acceptable enantioselectivities for all kinds of aldehydes can be observed when the chiral ligand (I) (or (I')) is used for catalyzing the synthesis of the asymmetric addition of trimethylsilyl cyanide to aldehydes to give optically active cyanohydrins, enantioselectivity more than 90% is rarely, if ever, observed. Ligands which can be used for catalyzing the synthesis of the asymmetric addition of trimethylsilyl cyanide to aldehydes to give optically active cyanohydrins with enantioselectivity greater than 90% are in high demand now.

SUMMARY OF THE INVENTION

The present invention relates to a novel chiral ligand of the formula (II)

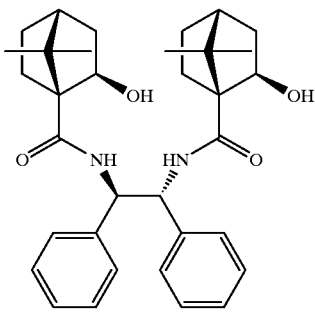

(II)

The organometallic complex catalyst formed from chiral ligand (II) and titanium tetraisopropxide could catalyze the addition of trimethylsilyl cyanide to give optically active cyanohydrin in the presence of molecular sieves 4 Å at −78° C. In addition, the used chiral ligands could be retrieved from the reaction mixture for recycling.

As used for catalyzing the synthesis of the asymmetric addition of trimethylsilyl cyanide to aldehydes to give optically active cyanohydrins, only catalytic amounts of the chiral ligand (II) of the present invention are required. The organometallic complexes catalyst containing the chiral ligand (II) of the present invention have acceptable enantioselectivities for all kinds of aldehydes. High enatnioselectivities, even higher than 90% can be observed for aliphatic aldehydes.

The present invention also relates to a novel diastereomer of the formula (II') of the chiral ligands of the formula (II):

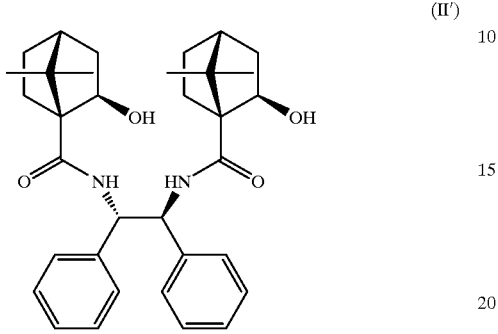

(II')

The synthesis and the application of the novel ligand (II') is very similar to those of the ligand (II). Anyone who is familiar with these arts can understand and derive the application and the synthesis of ligand (II') according to the application and the synthesis of ligand (II) disclosed in the description of the present invention.

DESCRIPTION OF THE PREFERRED EMBODIMENTS

The chiral ligand (II) of the present invention was synthesized by the following procedures. First, ketopinic acid chloride was used to react with trans-(1R,2R)-1,2-diphenyl ethylene diamine. After the product of the above reaction was purified, the carbonyl group of the purified product was further reduced to give the chiral ligand (II).

The ligand (II) of the present invention can be used for the synthesis of cyanohydrin by the following procedures: The chiral ligand (II) of the present invention was mixed with molecular 4 Å powders and titanium tetraisopropxide (Ti(O$^i$Pr)$_4$). After fully stirring, trimethylsilyl cyanide was added to the reaction mixture. After the temperature of the reaction mixture was cooled to −78° C., and the aldehyde was added into the reaction mixture. Optically active cyanohydrin can then be obtained through purification.

More detailed examples are used to illustrate the present invention, and these examples are used to explain the present invention. The examples below, which are given simply by way of illustration, must not be taken to limit the scope of the invention.

Preparation 1: the Preparation of Compound (III)

(1R,2R)-N,N'-bis[(1S,4R)-7,7-dimethyl-2-oxo-bicyclo[2.2.1]heptylcarboxyl]-N,N'-diphenyl ethylene diamine (III)

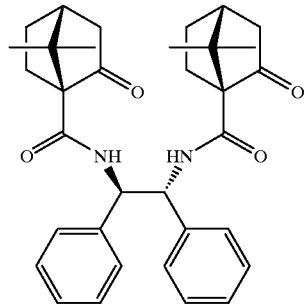

(III)

Ketopinic acid chloride (100.5 mmole) in CH$_2$Cl$_2$ was added to a stirred solution of trimethylamine (100 mmole), optically active trans-(1R,2R)-1,2-diphenyl ethylene diamine and CH$_2$Cl$_2$ (100 ml) at 0° C. over a 1 h period. After stirring for another 1 h, deionized water (100 ml) was added to the mixture. The mixture was neutralized and extracted with CH$_2$Cl$_2$. The CH$_2$Cl$_2$ layer was then washed with brine (2×200 ml), dried, filtered, concentrated and purified by column chromatography to furnish compound (III), as a white solid. Yield 95%.

$^1$H NMR (400 MHz, CDCl$_3$): δ8.48(d, J=6Hz, 2H), 7.10–7.22(m, 10H), 5.45(dd, J=2, 6Hz, 2H), 2.39–2.48(m, 2H), 1.96–2.08(m, 6H), 1.46–1.60(m, 2H), 1.36–1.43(m, 2H), 1.15(s, 6H), 0.87(s, 6H),

Analysis:
Calcd: C, 75.53; H, 7.46; N, 5.18
Found: C, 75.47; H, 7.43; N, 5.05

Preparation 2: the Preparation of Compound (II)

(1R,2R)-N,N'-bis[1S,2R,4R]-7,7-dimethyl-2-hydroxy-bicyclo [2.2.1]heptyl carboxyl]-N,N'-diphenyl ethylene diamine (II)

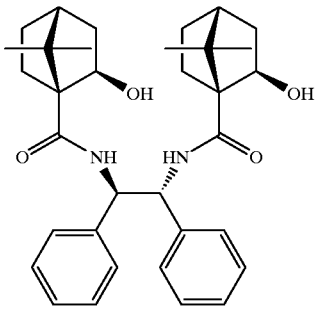

(II)

To a solution of (III) (4 mmole) in THF(5 ml) under argon at −78° C. was added 1 N L-selectride in THF(18.0 ml) dropwise. The reaction mixture was stirred at −78° C. for 2 h followed by 1 h at room temperature. Then the reaction mixture was cooled to 0° C. and quenched by the successive addition of EtOH (12 ml), 3 N aq. NaOH (16 ml), followed by the dropwise addition of 30% H$_2$O$_2$ (12 ml) over a 30 min. period. The aqueous phase was saturated with $K_2CO_3$ and extracted with $CH_2Cl_2$. The organic phase was dried with $Na_2SO_4$, and filtered. The $CH_2Cl_2$ layer was concentrated to furnish compound (II), as a white solid. Yield 95%.

$^1$H NMR (400 MHz, $CDCl_3$): δ7.86(d, J=8Hz, 2H), 7.16(m, 6H), 7.03(m, 4H), 5.39(d, J=8Hz, 2H), 5.29(dd, J=8, 4Hz, 2H), 3.89(m, 2H), 2.46(m, 2H), 1.94(m, 4H), 1.75(m, 4H), 1.06(m, 4H), 0.97(s, 6H), 0.80(s, 6H)

$^{13}$C NMR (100 MHz, $CDCl_3$): δ173.49(c), 137.83(c), 128.43(2CH), 127.48(CH), 126.94(2CH), 77.18(CH), 59.19 (CH), 58.21(C), 49.97(C), 45.17(CH), 40.94($CH_2$), 28.81 ($CH_2$), 26.26($CH_2$), 20.62($CH_2$), 20.47($CH_3$),

IR (KBr) vmax($cm^{-1}$):3366, 2936, 1642, 1545, 697.

Specific rotation: $[α]_D^{26}$=−170.52(c0.52, $CHCl_3$)

The following examples (1–3) are the applications of the chiral ligands of the present invention.

EXAMPLE 1

To a stirred solution of compound (II) (0.0897 g, 16.5 mol %) and molecular sieve 4 Å (powder, 65 mg, dehydrated under the condition of 0.3 mmHg/300° C. for 24 h before use) in dichloromethane (2.5 ml) was added titanium tetraisopropoxide (0.045 ml, 15 mol %) under argon at room temperature. Stir for 1 hour. Trimethylsilyl cyanide (0.15 ml, 1.1 mmol) was added to the reaction mixture and stirred for additional 0.5 h. Then, the reaction mixture was cooled to −78° C. and benzaldehyde (0.1 ml, 1 mmol) was added to the reaction mixture. The resultant reaction mixture was stirred for 48 h. The disappearance of the aldehyde was monitored by thin layer chromatography (ethyl acetate/hexane=1/5). The reaction mixture was quenched with 1 N HCl (10 ml) and stirred vigorously at room temperature for 6 h. After filtering, the mixture was extracted with dichloromethane (2×10 ml). The combined organic extracts were washed with brine (2×10 ml) and dried over anhydrous $Na_2SO_4$, then concentrated in vacuo. The residue was distilled under reduced pressure to afford 2-hydroxyl-2-phenylacetonitrile (87%, 93.2% e.e. (enantiomeric excess)). The result is listed in table 1.

EXAMPLES 2 to 3

The procedures and reagents used for preparing cyanohydrin in example 2 to 3 are as same as those in example 1 except the aldehydes in example 1 were replaced by the aldehydes listed in table 1. The results are also shown in table 1.

TABLE 1

| example | aldehyde | Cyanohydrin | Yield (%) | e.e (%) | Configuration |
|---|---|---|---|---|---|
| 1 | Benzaldehyde | 2-hydroxy-2-phenylacetonitrile | 87 | 93.2 | S |
| 2 | cyclo-hexanecarb-aldehyde | 2-cyclohexyl-2-hydroxy-acetonitrile | 90 | 100 | S |
| 3 | valeraldehyde | 2-hydroxy-hexylnitrile | 92 | 97.4 | S |

Comparative Examples 1 to 3

The procedures and reagents used for preparing cyanohydrin in comparative examples 1 to 3 are the same as those in example 1 except the compound (II) in example 1 was replaced by the compound (I) listed in table 2. The results are also shown in table 2.

TABLE 2

| example | aldehyde | cyanohydrin | Yield (%) | e.e (%) | Configuration |
|---|---|---|---|---|---|
| 1 | Benzaldehyde | 2-hydroxy-2-phenylacetonitrile | 79 | 94 | S |
| 2 | cyclo-hexanecarb-aldehyde | 2-cyclohexyl-2-hydroxy-acetonitrile | 94 | 87.2 | S |
| 3 | valeraldehyde | 2-hydroxy-hexylnitrile | 96 | 88.5 | S |

Comparing enantioselectivities listed in table 1 and table 2, it's easy to understand that the enantioselectivity of the ligand of the present invention is better than that of ligand (I) for acting as the catalyst of the addition of trimethylsilyl cyanide to benzaldehyde. In other words, the addition of trimethylsilyl cyanide to benzaldehyde by using the complex formed from titanium tetraisopropoxide [$Ti(O^iPr)_4$] and the ligand of the present invention as the catalyst is more enantioselective than using the complex formed from titanium tetraisopropoxide [$Ti(O^iPr)_4$] and ligand (I) as the catalyst.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A chiral compound of the formula (II) or formula (II'),

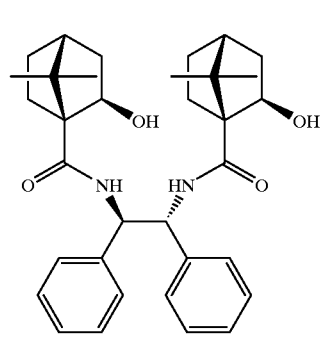

(II)

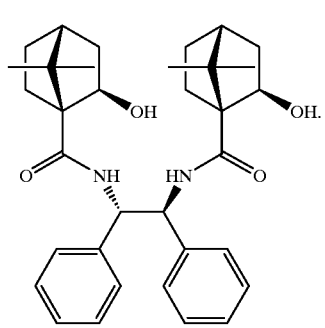

(II')

2. An organometallic catalyst complex comprising [$Ti(O^iPr)_4$] and the chiral compound of claim 1.

3. A method for preparing cyanohydrins from aldehydes, which is characterized by applying the organometallic catalyst complex of claim 2 as the catalyst to catalyze the addition of trimethylsilyl cyanide to aldehydes to give optically active hydroxylcyanides.

4. The process of claim 3, wherein the addition undergoes by using molecular sieve 4 Å.

5. The process of claim 3, wherein the aldehydes are aliphatic aldehydes.

* * * * *